United States Patent [19]

Cynamon et al.

[11] Patent Number: 5,643,912

[45] Date of Patent: Jul. 1, 1997

[54] PYRAZINOIC ACID ESTERS AS ANTI-MYCOBACTERIUM AVIUM AGENTS

[75] Inventors: Michael Henry Cynamon, Dewitt; John T. Welch, Albany, both of N.Y.

[73] Assignee: The Research Foundation of State University of NY, Albany, N.Y.

[21] Appl. No.: 584,707

[22] Filed: Jan. 11, 1996

Related U.S. Application Data

[63] Continuation of Ser. No. 169,308, Dec. 17, 1993, abandoned.

[51] Int. Cl.$^6$ .................... A61K 31/495; C07D 241/18
[52] U.S. Cl. ................................ 514/255; 544/406
[58] Field of Search ..................... 544/406; 514/255

[56] References Cited

U.S. PATENT DOCUMENTS

| | | | |
|---|---|---|---|
| 2,646,431 | 7/1953 | Dalalian | 544/406 |
| 2,677,641 | 5/1954 | Williams et al. | 514/255 |
| 4,051,245 | 9/1977 | Ambrogi et al. | 544/406 |
| 4,141,977 | 2/1979 | Yu et al. | 544/406 |
| 4,576,815 | 3/1986 | Robinson | 423/658.5 |
| 4,581,220 | 4/1986 | Nelson et al. | 423/658.5 |
| 4,961,856 | 10/1990 | Dalton et al. | 210/681 |
| 4,962,111 | 10/1990 | Welch et al. | 514/255 |
| 5,496,949 | 3/1996 | Toida et al. | 544/406 |

FOREIGN PATENT DOCUMENTS 1361967  7/1974  United Kingdom .

OTHER PUBLICATIONS

Grant & Hackh's Chemical Dictionary (5th Ed.) p. 24 (1987).
Organic Chemistry (3rd Ed) by Morrison and Boyd pp. 81–82 (1974).
Imperial Chemical Industries, *Chemical Abstracts*, vol. 101, No. 155555 (1984) (Abstract for JP59-100230, Jun. 9, 1984).
Dalton et al, *Chemical Abstracts*, vol. 112, No. 40123 (1990) (Abstract for EP 332314, Sep. 13, 1989).
Kushner, S. et al. "Experimental Chemotherapy of Tuberculosis, II., The Synthesis of Pyrazinamides and Related Compounds" *J. Am. Chem. Soc.* 74, 3617–3621 (1952).
Solomons, I. A. and Spoerri, P. E. "Esters of Pyrazionic and Pyrazine . . . " *J. Am. Chem. Soc.* 75, 679–681 (1953).
Kushner, S. et al., "Experimental Chemotherapy of Tuberculosis, III, Ethyl Mercaptan and Related Compounds in Tuberculosis" *J. Am. Chem. Soc.* 77, 1152–1155 (1954).
Brown, H. D. et all "The Antituberculosis Activity of Some Ethylmercapto Compounds" *J. Am. Chem. Soc.* 76, 3860 (1954).
Ul 'Yanova et al., *Chem. Abst.* 79, 125379t (1973).
Heifets, et al. "Pyrazinamide is not active in vitro against *Mycobacterium avium* Complex" *Am. Rev. Resp. Dis.* 134, 1287–1288 (1986).
Coker et al. "Clinical aspects of mycobacterial infections in HIV infection" *Res. Microbiol.* 377–381 (1992).
Cynammon, et al. "Antimycobactrial Activity of a Series of Pyrazinoic Acid Esters" *J. Med. Chem.* 1212–1215 (1991).
Wallace, et al. "Susceptibility Testing of Slowly Growing Mycobacteria . . . " *J. Clin. Microbiol.* 976–981 (1986).

*Primary Examiner*—Emily Bernhardt
*Attorney, Agent, or Firm*—Heslin & Rothenberg, P.C.

[57] ABSTRACT

Compounds of formula II

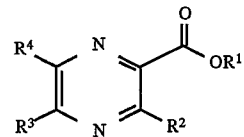

wherein $R^1$ is a hydrocarbon, halogenated hydrocarbon, polyether, substituted phenyl, substituted benzyl or alkylamine; and $R^2$, $R^3$ and $R^4$ are hydrogen, lower alkyl, halogen, haloalkyl, alkoxy and similar substituents are disclosed. The compounds are useful in the treatment of M. avium. Methods and compositions utilizing novel as well as known compounds are disclosed.

18 Claims, No Drawings

PYRAZINOIC ACID ESTERS AS ANTI-MYCOBACTERIUM AVIUM AGENTS

This invention was made with support from the Department of Veterans Affairs, from the National Science Foundation Grant Nos. CHE 8520875 and CHE 8901986, and from the National Institutes of Health Grant No. RO1 AI33690. The U.S. Government may have certain rights in the invention.

CROSS REFERENCE TO RELATED APPLICATIONS

This application is a continuation of earlier application, Ser. No. 08/169,308 filed Dec. 17, 1993 now abandoned, the entire disclosure of which is incorporated herein by reference.

FIELD OF THE INVENTION

This invention relates in general to the field of therapeutic agents for the treatment of mycobacterial infection, and more particularly to the use of pyrazinoic acid esters to treat infection by Mycobacterium avium and Mycobacterium avium-intracellulare complex.

BACKGROUND OF THE INVENTION

The goal of chemotherapy of mycobacterial infections is to stop the worsening of the disease, to convert secretions to a noninfectious state by killing the bacilli if possible, and to allow healing of gross pathological damage. Antimycobacterial agents are discussed at length in Medicinal Chemistry, Part I, Alfred Burger, ed. (Wiley-Interscience, N.Y. 1970), Chapter 19.

Pyrazinamide is known for the therapy of tuberculosis. The synthesis of pyrazinamide was described by Kushner et al, *J. Am. Chem. Soc.* 74:3617 (1952), and the compound was patented in 1954 as a tuberculostatic agent. Williams, U.S. Pat. No. 2,677,641. When pyrazinamide is used alone resistance develops quickly, and for this reason it is usually administered in combination with other drugs such as isoniazid. Another disadvantage of pyrazinamide is its hepatotoxicity.

Pyrazinamide is only active against Mycobacterium (M.) tuberculosis. It is not active against the closely related organism M. bovis or other mycobacteria. In particular, it has been reported to be inactive against M. avium [Heifets et al. *Am. Rev.. Resp. Dis.* 134:1287–1288 (1986)] which has become a serious cause of disseminated infection among patients with AIDS.

Other than our own earlier patent, (U.S. Pat. No. 4,962, 111), there is little or no support in the art for using pyrazinoic acid esters as tuberculostatic agents. U.S. Pat. No. 2,646,431 issued to Dalalian and Kushner covered pyrazine derivatives and methods of preparation. One such group of derivatives, thiolpyrazinoates, showed bacteriostatic and bacteriocidal properties against human tubercle bacillus. However, the specification states that in general, pyrazine monocarboxylic acid and derivatives such as esters do not possess bacteriostatic or bacteriocidal properties.

In 1954 Kushner et al. [*J. Am. Chem. Soc.* 77:1152–1155] reported the use of ethyl mercaptan and related compounds in experimental treatment of tuberculosis. Isopropyl thiopyrazinoate applied subcutaneously exhibited activity in a standardized mouse test. However, the authors attributed this activity to the release of ethyl mercaptan, not to the pyrazinoyl residue. Brown et al. [*J. Am. Chem. Soc.* 76:3860 (1954)] also reported that ethyl mercapto compounds had antituberculosis activity, thus supporting the Kushner et al. assertion that the activity of ethyl thiopyrazinoate was due to ethyl mercaptan and not the pyrazinoyl residue. The only suggestion that pyrazinoic acid esters might have some value in tuberculosis therapy is found in Solomons and Spoerri, [*J. Am. Chem. Soc.* 75:679 (1953)]. In the course of evaluating esters of pyrazinoic and pyrazine-2,3-dicarboxylic acids as local anesthetics, the authors learned of the effectiveness of pyrazinamide as a tuberculostatic agent. The authors tested their anaesthetic compounds for in vitro activity against Myobacterium tuberculosis H37RV and reported that a few were active, including N,N-dimethyl-2-aminoethyl pyrazinoate. No further work appears to have been done with this compound, and its effectiveness against other mycobacteria, including pyrazinamide-resistant M. tuberculosis, would not have been obvious on the basis of this isolated in vitro test.

In 1958, Suzuki et al. [Takamine Kenkyusho Nempo 10:19–23] reported that the pyrazinoate ester of chloramphenicol was inactive against a number of bacteria including M. tuberculosis.

It has now been surprisingly found that esters of pyrazinoic acid are active against the clinically important Mycobacterium avium complex. In exploring the breadth of operable esters, which appears to include all ester residues that can be cleaved to pyrazinoic acid by the target bacterium, many esters have been prepared within a novel genus of chemical compounds.

SUMMARY OF THE INVENTION

In one aspect, the invention relates to a method of treating a mammal infected with Mycobacterium avium comprising administering to the mammal an antibacterially effective amount of a compound of formula I or a pharmaceutically acceptable salt thereof:

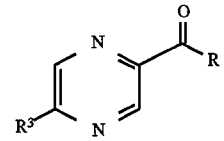

I wherein $R^3$ is hydrogen, methyl, trifluoromethyl or halogen and R represents the residue of an ester that can be cleaved by a mycobacterial esterase.

In particular the mammal may be treated with a compound of formula II or a pharmaceutically acceptable salt thereof:

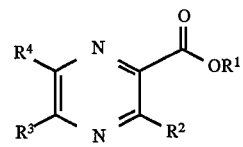

II wherein $R^1$ is:

(a) $C_1$ to $C_{20}$ hydrocarbon;

(b) $C_1$ to $C_{20}$ haloalkyl;

(c) alkoxyalkyl or alkoxypoly(alkoxy)alkyl;

(d) aryl of formula III:

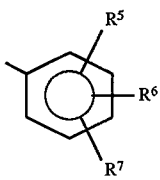

$R^5$, $R^6$ and $R^7$ independently are:
(1) Q, where Q is H, lower alkyl, haloalkyl, alkoxyalkyl, or phenyl;
(2) halogen;
(3) nitro;
(4) OQ;
(5) SQ;

(e) benzyl or substituted benzyl of formula III:

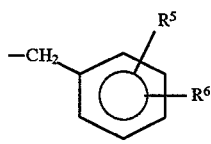

(f) a $C_1$ to $C_{20}$ alkylamine; (compounds having this residue will be O-esters of a $C_1$ to C20 hydroxylamine.)
$R^2$ is:
(a) H;
(b) lower alkyl;
(c) lower haloalkyl;
(d) halogen;
$R^3$ and $R^4$ independently are:
(a) H;
(b) lower alkyl;
(c) lower haloalkyl;
(d) halogen;
(e) OQ;
(f) SQ.

In preferred embodiments, $R^2$ and $R^4$ are hydrogen and $R^3$ is H, halogen, or trifluoromethyl. In various embodiments, $R^1$ may be fluoroalkyl, alkyl of 1 to 21 carbons, benzyl, alkenyl, alkoxypoly(alkoxy)alkyl or substituted phenyl, preferably phenyl substituted with hydrogen, phenyl, halogen, or lower alkyl.

In another aspect, the invention relates to a compound of formula IIa or a pharmaceutically acceptable salt thereof:

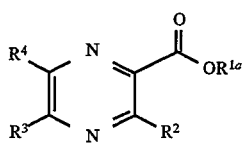

wherein $R^{1a}$ is:
(a) alkoxyalkyl or alkoxypoly(alkoxy)alkyl;
(b) $C_8$ to $C_{20}$ hydrocarbon;
(c) $C_8$ to $C_{20}$ haloalkyl;
(d) $C_1$ to $C_{20}$ alkylamine;
wherein $R^2$ is:
(a) H;
(b) lower alkyl;
(c) lower haloalkyl;
(d) halogen;

wherein $R^3$ and $R^4$ independently are:
(a) H;
(b) lower alkyl;
(c) lower haloalkyl;
(d) halogen;
(e) OQ, where Q is H, lower alkyl, haloalkyl, alkoxyalkyl or phenyl;
(f) SQ.

Preferred embodiments are those in which $R^2$ is hydrogen, $R^4$ is hydrogen or alkoxy, and $R^3$ is H, halogen, or trifluoromethyl, particularly halogen.

In various embodiments, $R^{1a}$ may be $C_8$ to $C_{20}$ alkyl, $c_{10}$ to $C_{20}$ hydrocarbon, alkoxyalkyl or alkoxypoly(alkoxy) alkyl, particularly alkoxyethoxyethyl, methoxyethoxyethyl and -N-(n-alkyl)amino.

In another aspect, the invention relates to a method of treating a mammal infected with a bacterium containing mycolic acid in its cell wall, comprising administering a non-toxic, antibacterially effective amount of a compound described above or a pharmaceutically acceptable salt thereof.

In another aspect, the invention relates to an antibacterial composition comprising a pharmaceutically acceptable carrier and a compound described above, which has activity against bacteria having mycolic acid in their cell walls. Alkyl as used herein refers to a saturated hydrocarbon residue that may be linear or branched. Cycloalkyl refers to a saturated hydrocarbon residue that is cyclic. Lower alkyl refers to linear or branched saturated hydrocarbons of one to four carbons. Lower cycloalkyl refers to cyclic saturated hydrocarbons of four or three carbons. The term "hydrocarbon" refers to all residues composed solely of hydrogen and carbon, including branched, cyclic, saturated and unsaturated residues.

DETAILED DESCRIPTION OF THE INVENTION

The compounds of the present invention are prepared from known starting materials via various procedures, for example, the method described below:

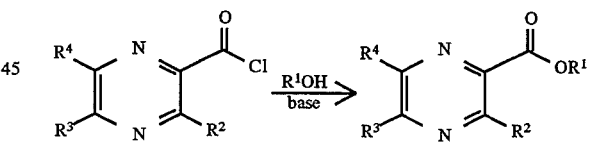

By this method an appropriately functionalized pyrazinoic acid is condensed, via the formation of the pyrazinoic acid chloride, with an alcohol to yield the desired esters. Other acyl-activating groups well known in the art may be similarly employed. Activation with trimethylsilyl chloride, described below as Procedure C, is an example of another such procedure.

Synthesis of Intermediates

Intermediate A: Pyrazinoyl chloride.

Pyrazinecarboxylic acid (3.7 g, 30 mmol), benzene (25 mL) and thionyl chloride (15 mL) were added into a 100 mL round bottom flask. The reaction mixture was heated under reflux for two hours after which time benzene and excess thionyl chloride were removed by distillation. The dark red crude pyrazinoyl chloride was purified by sublimation under vacuum at a bath temperature of 50°–60° C. to give colorless crystals that weighed 3.2 g (74% yield).

Intermediate B: 5-Chloro-2-pyrazinoyl chloride

5-Chloro-2-pyrazinecarboxylic acid, available from Lonza (Visp, Switzerland) was converted to the corresponding acid chloride as described for intermediate A.

Intermediate C: 5-Methyl-2-pyrazinoyl chloride

5-Methyl-2-pyrazinecarboxylic acid, available from Lonza (Visp, Switzerland) was converted to the corresponding acid chloride as described for intermediate A.

Synthesis of Esters

The general procedures for synthesizing esters were as follows:

Procedure A

Purified pyrazinoyl chloride or substituted pyrazinoyl chloride was transferred into a flask containing about 30 volumes of a 5% solution of pyridine in methylene chloride cooled to 0° C., and about one equivalent of the appropriate alcohol was added. (If the alcohol is inexpensive and volatile, a large excess can be used.) The reaction mixture was stirred at 0° C. for one hour, warmed to room temperature slowly and then stirred at room temperature for 12 to 48 hours. The reaction mixture was transferred to a separatory funnel and washed twice with aqueous copper sulfate solution followed by water and then brine solution. The methylene chloride layer was dried over magnesium sulfate and solvent evaporated. The residue was purified further by recrystallization from the solvent shown in the table or distilled (commonly in a Kugelrohr) at the boiling point shown in Table 1 to give the corresponding ester.

Procedure B

To a flame dried flask cooled under a nitrogen atmosphere containing the appropriate alcohol was added about 6 volumes of anhydrous tetrahydrofuran. To this solution with stirring at room temperature was added one equivalent of n-butyllithium (2.5 M in hexanes). After 30 minutes at room temperature, one equivalent of the appropriate pyrazinoyl chloride dissolved in 6 volumes of anhydrous tetrahydrofuran was added cautiously to the solution of the alkoxide. The reaction mixture was then heated under reflux for one hour. On cooling to room temperature the reaction mixture was poured onto one volume of water and the organic phase separated. The aqueous phase was extracted with diethyl ether; the combined organic phases were dried over anhydrous magnesium sulfate and concentrated in vacuo. The residue was purified by Kugelrohr distillation to yield the desired product.

Procedure C

One equivalent of pyrazinoic acid was dissolved or suspended in 20 volumes of the appropriate alcohol and 10 equivalents of trimethylsilyl chloride (TMSCl) were added. The mixture was stirred at room temperature for 48 hours and then stripped of solvent and excess TMSCl. The crude product was purified by chromatography on silica gel with a hexane-ethyl acetate gradient.

Transformations of Intact Esters

Procedure D

The appropriate 5-chloropyrazinoate, prepared as described elsewhere in Table 1, was dissolved in 10 mL per mmol of anhydrous acetonitrile. Three equivalents of silver (I) fluoride were added. The mixture was protected from moisture and was heated under reflux for 48 hours. After filtration and concentration in vacuo the residue was purified by Kugelrohr distillation to yield the desired fluorinated product.

Procedure E

The appropriate 5-chloropyrazinoate, prepared as described elsewhere in Table 1, was converted to the 5-iodo compound according to the method of Hirschberg and Spoerri *J. Org. Chem.* 26:1907–1912 (1961).

TABLE 1

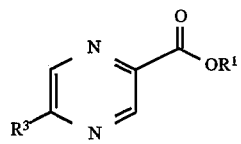

| Example | R¹ | R³ | Procedure | Yield % | mp/bp °C. | solvent/ pressure |
|---|---|---|---|---|---|---|
| 1 | n-decyl | H | A | 94 | 147–149 | 0.1 mm |
| 2 | n-pentadecyl | H | A | 83 | 46–48 | a |
| 3 | 4-fluorophenyl | H | A | 58 | 104–106 | b |
| 4 | 2,4,6-tribromophenyl | H | A | 66 | 158–160 | b |
| 5 | methyl | Cl | | Commercially available | | |
| 6 | n-decyl | Cl | A | 73 | 39–41 | c |
| 7 | n-pentadecyl | Cl | A | 69 | 57–59 | c |
| 8 | 2-octyl | Cl | A | 60 | 115 | 0.01 mm |
| 9 | -(CH₂CH₂O)₂CH₃ | Cl | A | 42 | 135 | 0.02 mm |
| 10 | -(CH₂CH₂O)₂CH₂CH₃ | Cl | A | 44 | 125 | 0.01 mm |
| 11 | -(CH₂CH₂O)₂(CH₂)₃CH₃ | Cl | A | 40 | 150 | 0.025 mm |
| 12 | -(CH₂CH₂O)₃CH₃ | Cl | A | 38 | 130 | 0.01 mm |
| 13 | n-hexyl | Cl | A | 71 | 125 | 0.015 mm |
| 14 | n-octyl | Cl | A | 91 | 158–160 | 0.025 mm |
| 15 | n-propyl | Cl | A | 92 | 93–95 | 0.05 mm |
| 16 | 7-tridecyl | Cl | B | 67 | 162 | 0.25 mm |
| 17 | 7-(7-methyl)tridecyl | Cl | B | 63 | 100 | 0.1 mm |
| 18 | n-heptyl | Cl | A | 79 | 140 | 0.2 mm |
| 19 | 2-decyl | Cl | A | 74 | 150 | 0.1 mm |
| 20 | n-nonyl | Cl | A | 72 | 165 | 0.1 mm |
| 21 | 2-(2-methyl)octyl | Cl | B | 72 | 155 | 0.025 mm |
| 22 | 2-(2-methyl)octyl | Cl | B | 67 | | |
| 23 | methyl | F | D | 93 | 53–55 | c |

TABLE 1-continued structure: pyrazine ring with $R^3$ at 5-position, carboxylate $C(O)OR^1$ at 2-position

| Example | $R^1$ | $R^3$ | Procedure | Yield % | mp/bp °C. | solvent/pressure |
|---|---|---|---|---|---|---|
| 24 | 2-heptyl | Cl | B | 76 | 130 | 0.1 mm |
| 25 | n-undecyl | Cl | A | 74 | 43–45 | c |
| 26 | n-pentyl | Cl | A | 82 | 105 | 0.1 mm |
| 27 | n-decyl | F | D | 91 | 105 | 0.05 mm |
| 28 | n-hexyl | F | D | 89 | 96 | 0.05 mm |
| 29 | 2-octyl | F | D | 94 | 96 | 0.1 mm |
| 30 | benzyl | Cl | A | 88 | 133–135 | 0.2 mm |
| 31 | n-butyl | Cl | A | 94 | 87–89 | 0.18 mm |
| 32 | 1-buten-3-yl | Cl | A | 78 | 85–90 | 0.2 mm |
| 33 | allyl | Cl | A | 91 | 88–90 | 0.1 mm |
| 34 | isobutyl | Cl | A | 90 | 88–90 | 0.18 mm |
| 35 | t-butyl | Cl | A | 55 | 95 | 0.1 mm |
| 36 | 2-undecyl | Cl | B | | | |
| 37 | 5-(5-methyl)dodecyl | Cl | B | | | |
| 38 | 5-(5-methyl)tridecyl | Cl | B | 32 | 120–122 | 0.25 mm |
| 39 | methyl | I | E | 70 | | |
| 40 | 5-(5-methyl)decyl | Cl | B | | | |
| 41 | 2,2,2-trifluoroethyl | H | A | 79 | 46–48 | a |
| 42 | allyl | H | A | | 72–74 | 0.25 mm |
| 43 | n-propyl | H | A | | 68–73 | 0.2 mm |
| 44 | 4-(4-methyl)nonyl | Cl | B | | | |
| 45 | 6-(6-methyl)undecyl | Cl | B | | | |
| 46 | 6-(6-methyl)dodecyl | Cl | B | | | |
| 47 | 6-(6-methyl)tridecyl | Cl | B | | | |
| 48 | 8-(8-methyl)heptadecyl | Cl | B | 98 | 160 | 0.25 mm |
| 49 | isobutyl | H | A | 65 | 83–85 | 0.1 mm |
| 50 | sec-butyl | H | A | 79 | 85–87 | 0.1 mm |
| 51 | 2,6-di-t-butyl-4-methylphenyl | H | A | 56 | 117–119 | b |
| 52 | benzyl | H | A | 84 | 119–121 | 0.05 mm |
| 53 | napthyl | H | A | 64 | 156–158 | b |
| 54 | (E)-crotyl | H | A | 80 | 85–87 | 0.05 mm |
| 55 | 2,4,6-trimethylphenyl | H | B | 54 | 78–80 | a |
| 56 | menthyl | H | A | 71 | 113–115 | 0.05 mm |
| 57 | n-heptyl | $CH_3$ | C | 95 | 147 | 0.25 mm |
| 58 | n-propyl | $CH_3$ | C | 89 | 91 | 0.25 mm |
| 59 | 10-nondecyl | Cl | B | | | |
| 60 | hexafluoroisopropyl | H | A | 72 | 72–73 | a |
| 61 | 2-bromoethyl | H | A | 62 | 98–100 | 0.05 mm |
| 62 | 2-chloroethyl | H | A | 57 | 83–85 | 0.05 mm |
| 63 | 4-nitrophenyl | H | A | 76 | 165–167 | b |
| 64 | 4-tolyl | H | A | 24 | 120–123 | a |
| 65 | 4-t-butylphenyl | H | A | 72 | 89–90 | a |
| 66 | pentafluorophenyl | H | A | 32 | 62–64 | b |
| 67 | 4-phenylphenyl | H | A | 39 | 95–98 | a |

Recrystalization solvents:
a hexanes
b hexane/ethyl acetate
c solvent not recorded Example 68. Formula II: $R^1$=$CH_3$; $R^2$=$R^3$=H; $R^4$=$OCH_3$ To 0.42 g (0.003 mol) of 6-hydroxy-pyrazinoic acid suspended in 10 mL of anhydrous methanol was added 4 mL of (0.030 mol) of chlorotrimethylsilane. The resultant mixture was allowed to stir for 48 hours at room temperature during which time the suspension became a solution. It is expected that this procedure may be used to convert 6-hydroxypyrazinoic acid to any 6-alkoxypyrazinoic ester by the use of the appropriate alcohol and, when the alcohol is not a liquid, the use of an inert solvent such as THF. The solvent and excess chlorotrimethylsilane were removed in vacuo by rotary evaporation. The crude product was purified by column chromatography on silica gel with a hexane-ethyl acetate gradient to yield 0.11 g (22%) of methyl 6-methoxypyrazinecarboxylate.

Example 69. Formula II: $R^1$=—$NH(CH_2)_7CH_3$; $R^2$=$R^3$=$R^4$=H

To a solution of 2.0 g (0.015 mol) of N-BOC-hydroxylamine in 25 mL of dimethylformamide is added 2.85 g (0.042 mol) of imidazole and 2.9 g (0.019 mol) of chloro-t-butyldimethylsilane. The reaction mixture is allowed to stir overnight at room temperature. The mixture is diluted with 30 mL of water and partitioned with 30 mL of dichloromethane. The organic phase is washed with three portions (20 mL) of brine. The organic layer is dried over anhydrous magnesium sulfate and concentrated in vacuo.

To 2.95 g (0.011 mol) of N-BOC-O-t-butyldimethylsilylhydroxylamine dissolved in 15 mL of anhydrous THF is added 0.264 g (0.011 mol) of sodium hydride. After stirring at room temperature for 30 minutes, to the solution of the resultant anion is added 2.00 g (0.011 mol) of n-octyl bromide. The reaction is allowed to stir overnight. The solution is diluted with 20 mL of water, and extracted with 30 mL (in 3 portions) of dichloromethane. The combined organic phases are dried and concentrated in vacuo.

To 1.85 g (0.005 mol) of N-BOC-N-octyl-O-t-butyldimethylsilylhydroxylamine dissolved in 20 mL of acetonitrile and 5 mL of water is added 1.3 g (0.0085 mol) of cesium fluoride. After 30 minutes the reaction mixture is diluted with an additional 20 mL of water and the product is extracted with 25 mL of dichloromethane. The combined organic phases are dried and concentrated in the usual manner. The product in this case is N-t-BOC-N-octylhydroxylamine; the process may be utilized to produce any desired N-protected alkylhydroxylamine from the corresponding alkyl bromide.

To a solution of 0.70 g (0.004 mol) of 5-chloro-pyrazinoyl chloride dissolved in dry acetonitrile (25 mL) is added dropwise at 0° C 1.0 g (0.004 mol) of N-BOC-N-octylhydroxylamine. The reaction mixture is allowed to stir overnight at room temperature. The solution is poured into 30 mL of water and extracted with 3 portions (10 mL each) of dichloromethane. The combined extracts are dried with magnesium sulfate and concentrated in vacuo. The crude product dissolved in 20 mL is treated with 3M HCl for 30 minutes at room temperature to remove the BOC group. On separation of the phases, drying and concentration the deprotected ester is purified by bulb-to-bulb distillation. An analogous procedure may be used to prepare other alkylhydroxylamine -O- esters by substituting the appropriate pyrazinoyl chloride and N-t-BOC alkylhydroxyamine.

Microbiological Testing of Compounds of the Invention

Methods employed for biological evaluation of the compounds were modified from Vestal, A. L., Procedures for isolation and identification of mycobacteria, P.H.S. Publication No. 1995, Laboratory Division National Communicable Disease Center, Atlanta, Ga., 1969. Mycobacteria were grown in Middlebrook 7H10 broth with OADC (oleic acid, dextrose, catalase) enrichment and 0.05% Tween 80 at pH 6.6. A Klett-Summerson colorimeter was used to standardize the cell suspensions using 7H10 broth as the diluent. Stock solutions of each pyrazinoic acid ester were prepared by dissolving a known weight of the agent in water or DMSO. The stock solutions were sterilized by passage through a 0.2 µm nylon membrane filter. Compounds were tested using an agar or broth dilution method, although only the results of the broth dilution testing are presented herein.

Broth dilution: Middlebrook 7H10 broth with OADC enrichment and 0.05% Tween 80 at pH 5.8 was prepared containing base 1 dilutions (256 µg/ml to 0.03 µg/ml) of the various esters. Each compound was tested in a 2 ml final volume. One hundred microliters of each cell suspension (for MTB 1K for other mycobacteria 0.1K) were added to yield approximately $5 \times 10^4$ CFU/ml. Tubes were evaluated visually to determine growth. The MIC is defined as the lowest concentration of drug that allows no detectable growth.

The compounds of the invention possess activity against clinical isolates of M. avium, M. kansasii and M. tuberculosis as shown in Table 2. In general, the compounds have activity against bacteria containing mycolic acid in their cell walls.

TABLE 2

In vitro activity of selected PAEs against Mycobacteria

| | MIC in µg/mL vs | | |
|---|---|---|---|
| Example # | M. avium 101 | M. kansasii SWK | M. tuberculosis 102 |
| 1 | 32 | 0.25 | 0.5 |
| 2 | 8[a] | 1 | 0.06 |
| 3 | 128 | 64 | 32 |
| 4 | 128 | 64 | 32 |
| 5 | 64[a] | 2 | 4 |
| 6 | 32 | 0.5 | 0.5 |
| 7 | >16 | 0.25 | 0.13 |
| 8 | 32 | <0.25 | <0.25 |
| 9 | 64 | 2 | 2 |
| 10 | 64 | 4 | 1 |
| 11 | 64 | 2 | 0.5 |
| 12 | 64 | 8 | 2 |
| 13 | 32 | <0.03 | 0.13 |
| 14 | 16 | <0.03 | 0.06 |
| 15 | 16 | 0.25 | 0.06 |
| 16 | 16 | 0.5 | 0.25 |
| 17 | 16[a] | 2 | 0.25 |
| 18 | 8 | <0.03 | 0.06 |
| 19 | 32 | 0.13 | 0.03 |
| 20 | 32 | <0.13 | <0.03 |
| 21 | 64 | 1 | 0.25 |
| 22 | 64 | 1 | 0.13 |
| 23 | 64 | 8 | 4 |
| 24 | 32 | <0.13 | 0.06 |
| 25 | 16 | 0.06 | 0.25 |
| 26 | 32 | 0.03 | 0.06 |
| 27 | 32 | 1 | 2 |
| 28 | 64 | 8 | |
| 29 | 32 | 0.03 | 2 |
| 30 | 8 | 1 | 1 |
| 31 | 64 | <1 | 0.25 |
| 32 | 64 | <1 | 2 |
| 33 | 64 | <1 | 1 |
| 34 | 64 | <1 | 2 |
| 35 | 128 | <1 | 2 |
| 36 | 16 | 0.25 | 0.25 |
| 37 | >64 | 16 | 8 |
| 38 | >64 | >16 | 16 |
| 39 | 256 | 8 | 16 |
| 40 | >256 | 16 | 4 |
| 41 | | 100 | 25[b] |
| 42 | | 3 | 6.3[b] |
| 43 | | 3 | 3[b] |
| 44 | >256 | 4 | 4 |
| 45 | >64 | 8 | 8 |
| 46 | >64 | 8 | 2 |
| 47 | >64 | | 2 |
| 48 | >64 | | 0.5 |
| 49 | 256 | 16 | 2 |
| 50 | 256 | 16 | 8 |
| 51 | >256 | >16 | 128 |
| 52 | 64 | 1 | 1 |
| 53 | 128 | >16 | 8 |
| 54 | | | 2 |
| 55 | 64 | 2 | 1 |
| 56 | | | 2 |
| 60 | | | 100[b] |
| 62 | | 25 | 6.3[b] |
| 63 | | 25 | 12.5[b] |
| 64 | | 100 | 100 |
| 65 | | 25 | 25 |
| 66 | | 25 | |
| 67 | | 25 | |

[a] in M. avium LPR
[b] in M. tuberculosis BUR

The pharmaceutical compositions containing the active ingredient may be in a form suitable for oral use, for example as tablets, aqueous or oily suspensions, dispersible powders or granules, emulsions, hard or soft capsules. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia, and lubricating agents, for example magnesium stearate, stearic acid or talc. The tablets may be uncoated or they may be coated by known techniques to delay disintegration and absorption in the gastrointestinal tract and thereby provide sustained action over a longer period.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth, and gum acacia; dispersing or wetting agents may be a naturally-occurring phosphatide, for example lecithin or condensation products of alkylene oxide with fatty acids, for example polyoxyethylene stearate, or condensation products of ethylene oxide with long chain aliphatic alcohols, for example heptadecethyleneoxycetanol, or condensation products of ethylene oxide with partial ester derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents such as sucrose or saccharin.

Oily suspensions may be formulated by suspending the active ingredient in a vegetable oil, for example such as arachis oil, olive oil, sesame oil or coconut oil, or in a mineral oil such as liquid paraffin. The oil suspensions may contain thickening agents, for example beeswax, hard paraffin or cetyl alcohol. Sweetening agents such as those set forth above, and flavoring agents may be added to provide a palatable oral preparation. These compositions may be preserved by addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleates. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. The suspension may be formulated according to the known art using those suitable dispersing and wetting agents and suspending agents which have been mentioned above. The sterile injectable preparation may also be a sterile injectable solution or suspension in a non-toxic parenterally-acceptable diluent or solvent, for example as a solution in 1,3-butanediol. Among acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition fatty acids such as oleic acid find use in the preparation of injectables.

What is claimed is:

1. A compound of formula IIa or a pharmaceutically acceptable salt thereof:

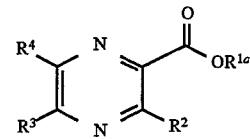

wherein $R^{1a}$ is:
  (a) loweralkoxyloweralkyl;
  (b) —$(CH_2CH_2O)_n$loweralkyl, wherein n is 2 or 3
  (c) —$NHR^{1b}$ where $R^{1b}$ is $C_1$ to $C_{20}$ alkyl;
$R^2$ is:
  (a) H;
  (b) lower alkyl;
  (c) lower haloalkyl;
  (d) halogen;
$R^3$ and $R^4$ independently are:
  (a) H;
  (b) lower alkyl;
  (c) lower haloalkyl;
  (d) halogen;
  (e) OQ, where Q is H, lower alkyl, or phenyl;
  (f) SQ.

2. A compound according to claim 1 wherein $R^4$ is H.

3. A compound according to claim 2 wherein $R^2$ is H.

4. A compound according to claim 3 wherein $R^3$ is H, halogen, or trifluoromethyl.

5. A compound according to claim 4 wherein $R^3$ is halogen.

6. A compound according to claim 4 wherein $R^{1a}$ is loweralkoxyloweralkyl or —$(CH_2CH_2O)_n$loweralkyl.

7. A compound according to claim 6 wherein $R^{1a}$ is alkoxyethoxyethyl.

8. A compound according to claim 6 wherein $R^{1a}$ is methoxyethoxyethyl.

9. A compound according to claim 4 wherein $R^{1a}$ is —$NHR^{1b}$.

10. A method of treating a mammal infected with a bacterium containing mycolic acid in its cell wall, comprising administering to said mammal a non-toxic, antibacterially effective amount of a compound according to claim 1 or a pharmaceutically acceptable salt thereof.

11. A method of treating a mammal infected with a bacterium containing mycolic acid in its cell wall, comprising administering to said mammal a non-toxic, antibacterially effective amount of a compound according to claim 5 or a pharmaceutically acceptable salt thereof.

12. A method of treating a mammal infected with a bacterium containing mycolic acid in its cell wall, comprising administering to said mammal a non-toxic, antibacterially effective amount of a compound according to claim 6 or a pharmaceutically acceptable salt thereof.

13. An antibacterial composition comprising a pharmaceutically acceptable carrier and a compound according to claim 1, said compound possessing activity against bacteria having mycolic acid in their cell walls.

14. An antibacterial composition comprising a pharmaceutically acceptable carrier and a compound according to claim 5, said compound possessing activity against bacteria having mycolic acid in their cell walls.

15. An antibacterial composition comprising a pharmaceutically acceptable carrier and a compound according to claim 6, said compound possessing activity against bacteria having mycolic acid in their cell walls.

16. An antibacterial composition comprising a pharmaceutically acceptable carrier and a compound of formula:

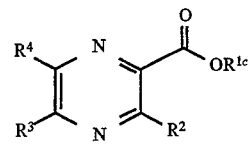

IIa wherein $R^{1c}$ is:

(a) loweralkoxyloweralkyl or —$(CH_2CH_2O)_n$loweralkyl, wherein n is 2 or 3;

(b) $C_{10}$ to $C_{15}$ alkyl;

(c) —$NHR^{1b}$ where $R^{1b}$ is $C_1$ to $C_{20}$ alkyl;

$R^2$ is:

(a) H;

(b) lower alkyl;

(c) lower haloalkyl;

(d) halogen;

$R^3$ and $R^4$ independently are:

(a) H;

(b) lower alkyl;

(c) lower haloalkyl;

(d) halogen;

(e) OQ, where Q is H, lower alkyl, or phenyl;

(f) SQ, said compound possessing activity against bacteria having mycolic acid in their cell walls.

17. n-Decyl 2-pyrazinoate or pharmaceutically acceptable salt thereof.

18. n-Pentadecyl 2-pyrazinoate or pharmaceutically acceptable salt thereof.

* * * * *